US009066882B2

(12) United States Patent
Venkataraman et al.

(10) Patent No.: US 9,066,882 B2
(45) Date of Patent: Jun. 30, 2015

(54) METHOD AND A SYSTEM FOR PRODUCING THERMOLABILE NANOPARTICLES WITH CONTROLLED PROPERTIES AND NANOPARTICLES MATRICES MADE THEREBY

(75) Inventors: Chandra Venkataraman, Mumbai (IN); Amol Ashok Pawar, Mumbai (IN)

(73) Assignee: INDIAN INSTITUTE OF TECHNOLOGY, BOMBAY, Mumbai (IN)

( * ) Notice: Subject to any disclaimer, the term of this patent is extended or adjusted under 35 U.S.C. 154(b) by 0 days.

(21) Appl. No.: 13/554,798

(22) Filed: Jul. 20, 2012

(65) Prior Publication Data

US 2013/0035279 A1 Feb. 7, 2013

(30) Foreign Application Priority Data

Aug. 4, 2011 (IN) ........................ 2213/MUM/2011

(51) Int. Cl.
| | |
|---|---|
| *A61K 9/51* | (2006.01) |
| *B82Y 40/00* | (2011.01) |
| *A61K 8/11* | (2006.01) |
| *B01J 13/04* | (2006.01) |
| *A61K 8/36* | (2006.01) |
| *A61Q 19/00* | (2006.01) |
| *A61K 8/02* | (2006.01) |
| *B82Y 5/00* | (2011.01) |

(52) U.S. Cl.

CPC ............ *A61K 9/5123* (2013.01); *A61K 9/5192* (2013.01); *B82Y 5/00* (2013.01); *B82Y 40/00* (2013.01); *A61K 8/11* (2013.01); *B01J 13/04* (2013.01); *A61K 8/361* (2013.01); *A61Q 19/00* (2013.01); *A61K 8/025* (2013.01); *A61K 8/0279* (2013.01); *A61K 8/0283* (2013.01); *A61K 2800/10* (2013.01); *A61K 2800/412* (2013.01); *A61K 2800/413* (2013.01); *A61K 2800/56* (2013.01); *A61K 2800/652* (2013.01)

(58) Field of Classification Search
None
See application file for complete search history.

(56) References Cited

U.S. PATENT DOCUMENTS

| | | | | | |
|---|---|---|---|---|---|
| 4,695,248 | A * | 9/1987 | Gray | ............................... | 432/58 |
| 2008/0102128 | A1* | 5/2008 | Constancis et al. | ........... | 424/489 |
| 2008/0268060 | A1* | 10/2008 | Nguyen et al. | ................ | 424/489 |
| 2009/0186757 | A1* | 7/2009 | Adiga | ........................... | 502/401 |
| 2010/0104625 | A1* | 4/2010 | Putnam et al. | ................ | 424/450 |

OTHER PUBLICATIONS

Pokryvailo et al., "High-Power Pulsed Corona for Treatment of Pollutants in Heterogeneous Media," Plasma Sci. 34:1731-1743 (2006).*
Eerikainen, et al., "Aerosol flow reactor method for synthesis of drug nanoparticles," Eur. J. Pharm. Biopharm. 55:357:360 (2003).*
Eerikainen, et al., "Preparation of polymeric nanoparticles containing corticosteroid by a novel aerosol flow reactor method," Intl. J. Pharm. 263:69-83 (2003).*
Pawar et al., "Droplet-Phase Synthesis of Nanoparticle Aerosol Lipid Matrices with Controlled Properties," Aerosol Sci. Tech. 45:811-820 (2011).*

Raula, et al., "Influence of the solvent composition on the aerosol synthesis of pharmaceutical polymer nanoparticles," Intl. J. Pharm. 284:13-21 (2004).*

Pawar et al., "Droplet-Phase Synthesis of Nanoparticle Aerosol Lipid Matrices with Controlled Properties," Aerosol Science and Technology 45:811-820 (first available online Mar. 2011).*

Weiss et al., "Solid Lipid Nanoparticles as Delivery Systems for Bioactive Food Components," Food Biophysics 3:146-154 (2008).*

Surajit Das et al., "Recent Advances in Lipid Nanoparticle Formulations with Solid Matrix for Oral Drug Delivery", AAPS PharmSciTech, vol. 12, No. 1, pp. 62-76, Mar. 2011.

First Examination Report (FER) to Indian Application No. 2213/MUM/2011 dated Mar. 26, 2014.

* cited by examiner

*Primary Examiner* — James H Alstrum Acevedo

*Assistant Examiner* — Thea D' Ambrosio

(74) *Attorney, Agent, or Firm* — Novak Druce Connolly Bove + Quigg LLP

(57) ABSTRACT

This disclosure relates to a method and a system of producing nanoparticles and nanoparticle matrices of thermolabile, biocompatible matrix materials, like lipids and biopolymers with controlled properties. A prototype pulse-heat aerosol system is described for single-step production of free, thermolabile nanoparticles with sufficient control over size, morphology and crystallinity with controlled-release properties, for possible therapeutic, cosmetic or diagnostic use. Nanoparticles of the range 50 to 500 nm are obtained and are found suitable for controlled drugs delivery.

16 Claims, 4 Drawing Sheets

METHOD AND A SYSTEM FOR PRODUCING THERMOLABILE NANOPARTICLES WITH CONTROLLED PROPERTIES AND NANOPARTICLES MATRICES MADE THEREBY

This application claims priority to Indian application no. 2213/Mum/2011, filed Aug. 4, 2011. The disclosure set forth in the referenced application is incorporated herein by reference in its entirety.

TECHNICAL FIELD OF DISCLOSURE

This disclosure relates to a method producing thermolabile nanoparticles with controlled properties which could be used for therapeutic, cosmetic and diagnostic purposes. This disclosure also includes a system or device for producing such particles by pulse-heat aerosol method. Nanoparticles matrices prepared by this method are also included in this disclosure.

BACKGROUND

The controlled-release of drugs, their targeting to specific sites in the human body and the protection of delicate bioactive agents is desirable for efficient drug delivery. One approach towards achieving these ends involves encapsulating bioactive agents in biocompatible nanoparticle matrices. Control is needed over particle size and size distribution, substructure, crystallinity and thickness of encapsulating shell. Among matrix materials, polymers are not approved by the US-FDA for intravenous or pulmonary applications, because of toxic or allergenic end products from their metabolism, while liposomes are limited by low physical stability and high cost. Lipid nanoparticles, made from physiological lipids, like fatty acids and triglycerides, have shown promise in cellular/tissue targeting, sustained/controlled-release, enhancing solubility of poorly water-soluble drugs, and protection of susceptible therapeutic agents for example: Proteins, peptides, and nucleic acid. Their longer circulation time, in the human system, and higher drug payload have been exploited for treating diseases like cancer and brain disorders.

Preparation of nanoparticle drug matrices from processing of delicate, thermolabile materials, like lipids, including fatty acids and triglycerides, and other materials, including waxes and polymers (polylactides, polycyanoacrylates alginates, chitosan and gelatin), needs to address thermal and shear stress imposed, in addition to complexity (multiple steps, use of high or reduced pressure, cryogenic conditions) and cost. For example, current methods of production of lipid nanoparticles can be categorized as top-down methods such as emulsion based techniques (emulsification-solvent-evaporation; solvent emulsification-diffusion; warm w/o/w microemulsion-based techniques), and high pressure homogenization (hot/cold); and bottom-up methods based on supercritical fluids. Spray-drying and an aerosol reactor method are emerging bottom-up techniques, used at temperature of 100-250° C. to process crystalline drugs, polymers and proteins with high melting points.

Top-down method suffer limitations including imposition of thermal and shear stress, use of surface-active agents, use of high energy intensity and multiple post-processing steps. Emulsion based methods have been used to produce lipid and polymeric nanoparticles containing anti-cancer drugs like Doxorubicin and Podophyllotoxin, while high pressure homogenization has been used to prepare lipid nanoparticles containing protein with high structural stability and stronger internal coherence, such as cyclosporine A and lysozymes. Emulsion based methods often use ultrasonication resulting in high shear, cavitation and collision and large amount of surface-active agents to stabilize dispersion. In lipid-melt based methods, the amount of drug encapsulation is limited by its solubility in the lipid melt and the stability of the nano-emulsion. High-pressure and high shear homogenization are energy intensive. Both types of approaches need multiple post-processing steps including separation, filtration, drying, removal of residual organic solvents and lyophilization which increases manufacturing cost. In addition, there is poor control over properties of nanoparticles leading to phase-changes during shelf-life, drug-expulsion or burst-release kinetics, thermal degradation of the thermolabile active agents, insufficient control over particle size and large surfactant content causing greater cytotoxicity or lower absorption (Bunjes 2010).

Bottom-up methods include those based on super-critical fluid technology [Rapid expansion of supercritical solution (RESS), Gas antisolvent solution (GAS), solution enhanced dispersion with supercritical fluids (SEDS), Supercritical fluid extraction of emulsion (SFEE), particle formation from gas-saturated solutions (PGSS) and Rapid expansion of a supercritical solution into a liquid solvent (RESOLV)], nano-precipitation, self-assembly of polymeric micelles, spray drying and spray-freeze drying. The use of supercritical fluid technology is limited by the solubility of matrix and drug molecules in supercritical fluids/anti solvents and their denaturing effects on therapeutic macromolecules like proteins and peptides. In addition, there is high manufacturing complexity (maintaining system temperature and pressure above critical point) and production cost (sophisticated instrumentation).

Spray drying, used for generation of micron and sub-micron sized particles requires high temperature, of the order of 150° C. to remove the solvent from the atomized solution drop. In a recently reported study, a commercial spray dryer, equipped with a piezoelectric oscillating element, was employed for production of nanoparticles using a structurally stable protein like bovine serum albumin. Controlling precursor (solute and surfactant concentration) and process (spray mesh size, drying airflow rate and inlet temperature) parameters led to control over size (540-2609 nm diameter) and shape. Protein or peptide particles generated by this techniques often form aggregates; control over particle size is difficult.

An aerosol reactor method to produce micrometer to nanometer sized particles for drug applications uses a heated-wall aerosol flow reactor at temperature of 100-250° C., to process pure crystalline drugs, polymers and drug particles coated with a crystalline excipients. Precursor drugs, excipients and polymers processed by this method had melting temperature in the range of 200-800° C.

In summary, current methods of producing drug-containing nanoparticles include "Top down" and "Bottom-up" methods. Top-down methods are emulsion based techniques and employ high pressure homogenization. The technique suffers from the limitations of high energy intensity and imposition of high thermal and shear stress. Emerging bottom-up methods like spray drying and aerosol reactor method are suitable for production of crystalline drugs, polymers and proteins with high melting points. These methods have limitations in achieving control of target properties like size, crystallinity and control drug-release characteristics.

SUMMARY

An object of this disclosure is to produce thermolabile nanoparticles with sufficient control over size, morphology, crystallinity and controlled-release properties.

Another object of this disclosure is to produce such particles in a single step, continuous process through pulse-heat aerosol process by the application of a heat pulse of predetermined temperature and duration followed by thermal quenching.

DETAILED DESCRIPTION

Nanoparticles matrices of this disclosure are prepared by pulse-heat aerosol reactor method, which involves atomizing a liquid precursor solution containing thermolabile compounds (e.g. encapsulating matrix agents like lipids and/or biodegradable polymers and bioactive agents like drugs, proteins, peptides, nucleic acids, or combination thereof) into a carrier gas, subjecting the aerosol to a heat pulse of controlled magnitude and duration, followed by quenching with cold gas, and collecting the nanoparticles produced. The evaporation rate control thus achieved is used to obtain nanoparticle matrices with varying size, morphology and crystallinity, which have controlled-release properties. The devices consist of atomizer, pump, modular aerosol reactor enabling pulse-heating and means for quenching and temperature sensor.

This disclosure includes nanoparticle matrices prepared by using this device. It also includes encapsulation of drugs and other bioactives in the nanocapsule during the process of manufacture.

DETAILED DESCRIPTION WITH REFERENCE TO THE FIGURE OF THE SYSTEM FOR MAKING NANOPARTICLES MATRICES OF DISCLOSURE

The following specific example is not intended to be limitive but only illustrative.

Figure 1:
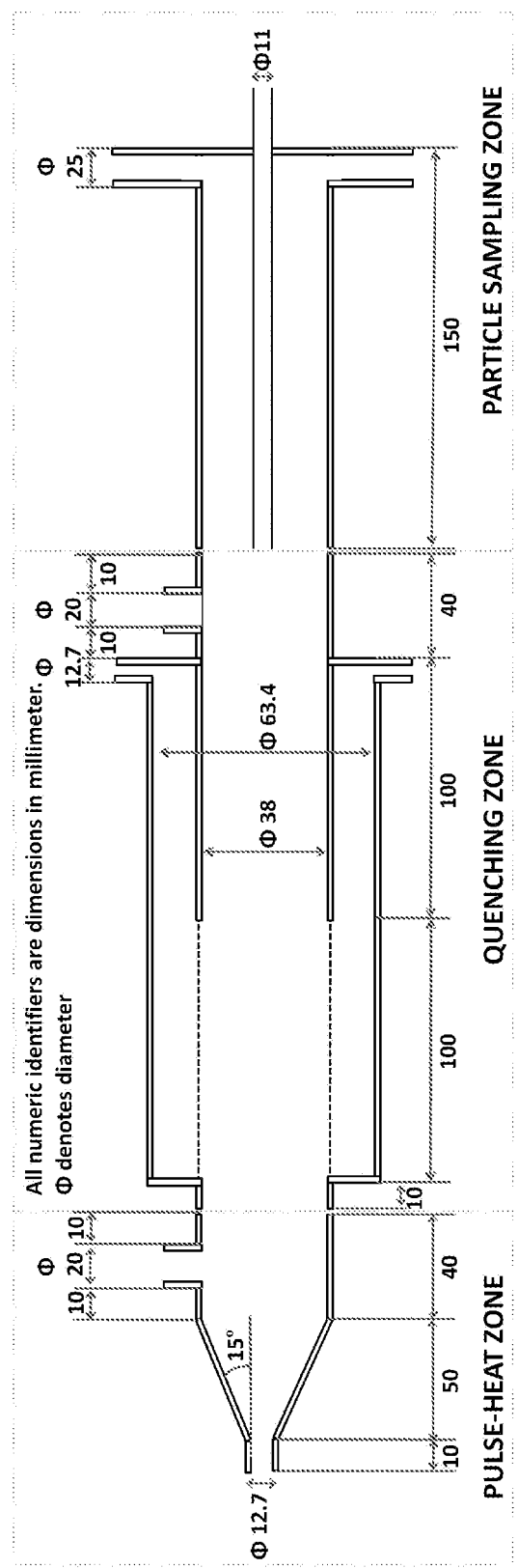
FIG. 1: Schematic diagram of the pulse-heat aerosol reactor (PHAR) system used for synthesis of nanoparticle matrices with controlled properties comprised a pulse-heating zone followed by a perforated diluter and an isoaxial sampler. The key variables in aerosol reactor design were maintaining laminar flow of the aerosol and minimizing particle losses by diffusion and sedimentation and provision for imposing pulse-heat with alternate heating and quenching by dilution air. (All dimensions in millimeters).
Figure 2:
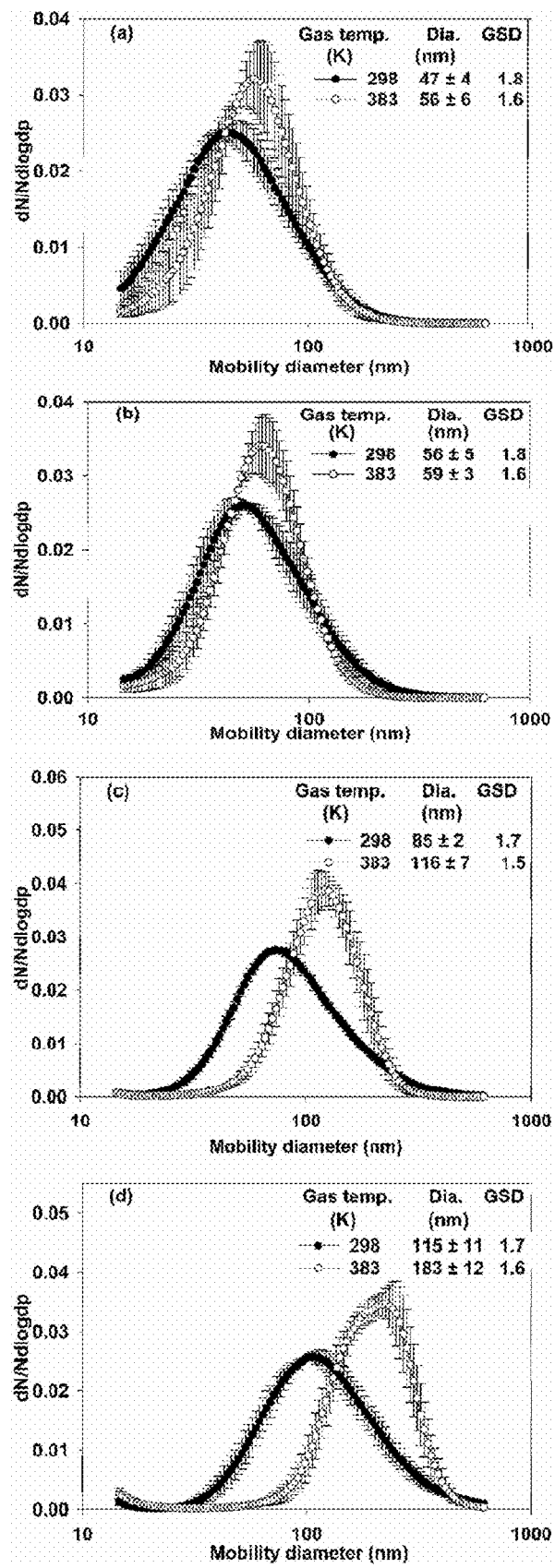
FIG. 2: Number particle size distributions of nanoparticle aerosol lipid matrices synthesized using stearic acid in cyclohexane solutions at gas temperature of 298 K and 383 K (pulse), of varying concentrations, (a) 0.01 mg·cm$^{-3}$, (b) 0.1 mg·cm$^{-3}$, (c) 1 mg·cm$^{-3}$ and (d) 10 mg·cm$^{-3}$, measured using scanning mobility particle sizer. The mobility diameters ranged from 47-183 nm with a unimodal distribution and geometric standard deviation of 1.5-1.8.

FIG. 1, a prototype pulse-heat aerosol reactor (PHAR) was designed and fabricated for control of particle properties through aerosol dynamics. The pulse-heating zone has an internal diameter and heated length of 38 mm and 80 mm, respectively. The aerosol flow rate was fixed at 3 L·min-1, with a flow Reynolds number of ~109 and a pulse time of one second. Stokes number for atomized droplets (mean diameter 300 nm) flowing in the reactor is in the order of $10^{-5}$, implying that droplets follow gas streamlines and do not undergo impaction. Evaporating droplets flowing along with the gas streamlines are expected to undergo negligible drop breakup, internal solute circulation/motion and asymmetric solute concentration distribution. Thus the droplet evaporation process is expected to be uniform leading to isotropic particle properties. In the prototype PHAR, heating was provided to the pulse-heat zone to attain a gas temperature of (low and high 383±1 K) using heating tape of 250 W. Gas temperature in the pulse-heat zone was measured using a platinum resistance temperature detector (RTD, PT100) interfaced with a digital controller. The magnitude of temperature was fixed based on the required evaporation rate to produce particles of different morphology and size, as described in a following section. In order to quench the aerosol, rapid cooling was applied following the pulse-heat zone, by diluting with dry nitrogen (298 K), with the ratio of 1:11, in a perforated-wall diluter of stainless steel (inner diameter 38 mm and length 250 mm). To ensure uniform and complete mixing of aerosols with dilution gas, the perforated-wall diluter comprised of 400 holes of 2 mm diameter each drilled at regular intervals upto a length of 100 mm. The diluted aerosol flow rate is 33 L·min$^{-1}$, with a flow Reynolds number of ~1199. The total loss of particles due to diffusion and sedimentation, in the PHAR, is estimated to be less than 1%.

Solutions of encapsulating agents like lipids (e.g. but not limited to stearic acid, palmitic acid, trimyristin), biopolymers (e.g. but not limited to poly-lactic-co-glycolic acid (PLGA), polymethacrylic copolymers), with surface active additives like sodium cholate, phosphatidylcholine and selected drug/s in organic solvents (e.g. but not limited to cyclohexane, chloroform and dichloromethane).

The disclosure can be employed as a single-step method for production of nanoparticle matrices, with controlled diameter (50-200 nm), morphology or structure (solid versus shell), crystallinity and controlled-release properties. To fix operating conditions for evaporation rate control in the PHAR, a stationary drop model was developed (Shetty et al. 2011). The difference in required evaporation rate to achieve solid versus shell morphology was estimated to be around a factor of five. Compute evaporation rates of stearic acid in cyclohexane solution drops (300 nm mean droplet diameter) of varying concentrations (0.01-10 mg·cm$^{-3}$) led to at gas temperature control at 298 K and 383 K (pulse).

Applications Include the Following:

Production of nanoparticle lipid matrices containing anti-cancer drugs for intravenous cancer chemotherapy for enhanced penetration and retention effects in tumor tissues, leading to improved efficacy of treatment.

Production of nanoparticle lipid matrices for controlled-release and pulmonary targeting applications. Drugs of interest may include anti-cancer drugs (e.g. Gefitinib), anti-diabetics (e.g. insulin), anti-tubercular drugs, therapeutics based on biotechnology derived products (like proteins, peptides, nucleic acids, vaccines, antibiotics) for treatment of various diseases and disorders.

Example Illustrating the Disclosure

Figure 4:
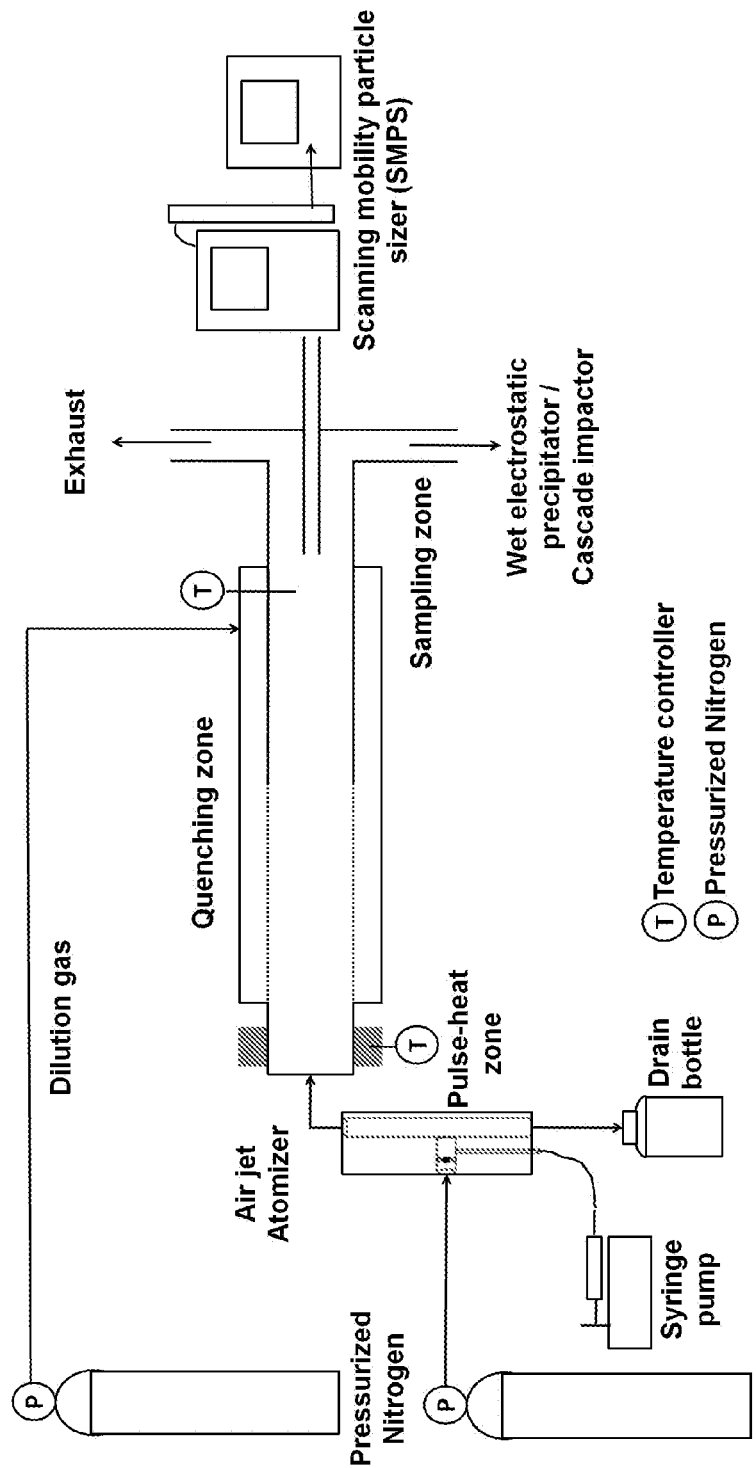
FIG. 4: Schematic diagram of the pulse-heat aerosol reactor (PHAR) system used for synthesis of nanoparticle matrices with controlled properties comprised of a collision-type air jet atomizer, a pulse-heating zone followed by a perforated diluter, and a scanning mobility particle sizer (SMPS) for measurement of mobility diameter. The key variables in aerosol reactor design were maintaining laminar flow of the aerosol and minimizing particle losses by diffusion

Experiments were done to produce stearic acid nanoparticles, in PHAR, with controlled size and morphology at varying evaporation rates. The pulse-heat aerosol reactor (PHAR) system used to study effect of pulse-heat on synthesis of nanoparticle matrices (FIG. 4) comprises of a collision-type air jet atomizer. The atomization device could also comprise of any device based on ultrasonic, electro spray, evaporation-condensation or FEAG principle of aerosol generation. The PHAR is designed with a pulse-heat zone, wherein a heat pulse of controlled temperature (heating element) and duration (flowrate of gas) is applied to the droplet aerosol to control the rate of evaporation. A perforated-wall aerosol diluter is provided to quench the temperature and aerosol dynamics mechanisms immediately after the pulse-heating. A scanning mobility particle sizer was placed downstream for measurement of mobility diameter. Any other nanoparticle size distribution measurement device including, ELPI, hypersonic impactor can be used in-lieu of or in addition to the SMPS. The standard upstream pressure of the atomizer was 35 psig. The solution, of lipid in a selected organic solvent (stearic acid in cyclohexane of varying concentrations, 0.01 mg·cm$^{-3}$, 0.1 mg·cm$^{-3}$, 1 mg·cm$^{-3}$ and 10 mg·cm$^{-3}$), was fed with a syringe pump at a flow rate of 0.6 mL/min. The resulting atomized droplets were suspended in a nitrogen flow through the PHAR, where droplet evaporation at a controlled rate, followed by quenching of aerosol dynamics was used to produce nanoparticles with controlled size, morphology and crystallinity.

Figure 3:
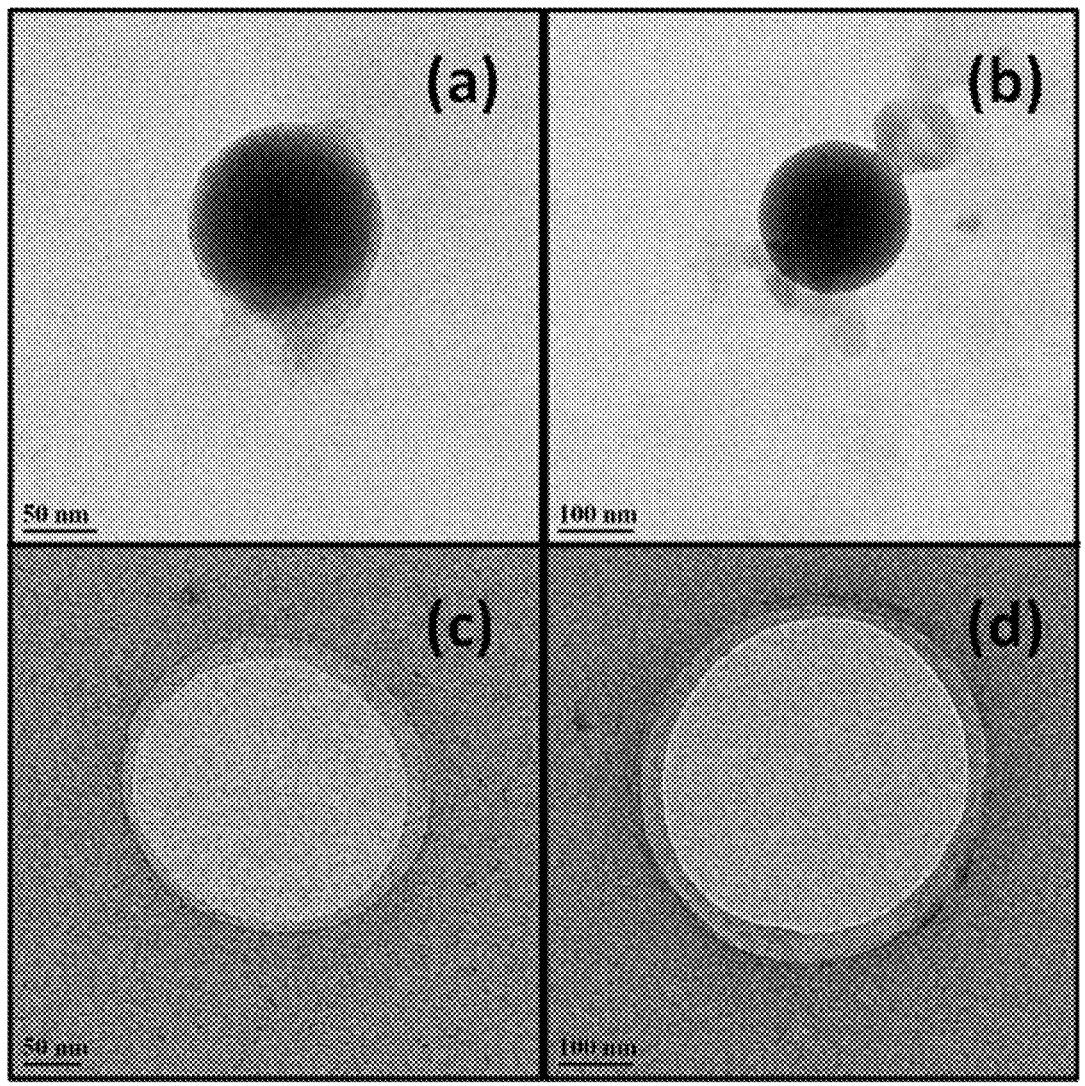
FIG. 3: FEG-TEM images of nanoparticle matrices, synthesized using stearic acid in cyclohexane solution of 10 mg·cm$^{-3}$, at gas temperatures of (a-b) 298 K and (c-d) 383 K pulse.

Stearic acid nanoparticle matrices of mobility diameters of 47-183 nm, with a unimodal size distribution of geometric standard deviations (GSD) (1.5-1.8), were obtained in PHAR by fixing the gas temperatures, at 298 K and 383 K (pulse), to obtain the varying evaporation rates. For a given concentration, stearic acid nanoparticles of smaller mobility diameters were synthesized at lower evaporation rates, while nanoparticles with larger mobility diameters were synthesized at higher evaporation rates. The differences in the mean mobility diameters of stearic acid nanoparticles synthesized at higher evaporation rates, using larger concentrations (1 mg·cm$^{-3}$ and 10 mg·cm$^{-3}$), were statistically significant (at the 95% confidence level; P=0.002, by t-test) than those synthesized at lower evaporation rates (Table 1). TEM images of nanoparticle matrices (FIG. 3a), synthesized at 298 K using stearic acid in cyclohexane solution of 10 mg·cm$^{-3}$, showed solid particles of ~150 nm diameters with smooth spherical shape. On contrary, TEM images of nanoparticle matrices (FIG. 3b), synthesized at 383 K (pulse) using stearic acid in cyclohexane solution of 10 mg·cm$^{-3}$, showed hollow or shell particles of ~300 nm diameter with spherical shape. The differences in the mean mobility diameters of synthesized, at higher evaporation rates, by pulse-heat (383 K), using larger concentrations (1 mg·cm$^{-3}$ and 10 mg·cm$^{-3}$), were statistically significant (at the 95% confidence level; P=0.002, by t-test) than those synthesized at lower evaporation rate (298 K). This reveals the formation of spherical solid particles at 298 K, but hollow or shell-like particles at 383 K (pulse).

The following tables show computational values for evaporation rate, drop temperature, time for onset of crystallization, drop size at onset of crystallization and evaporation time# and experimental results for measured mobility diameter.

TABLE 1

| | | Modeling results | | | Experimental results | |
|---|---|---|---|---|---|---|
| Concentration (mg · cm$^{-3}$) | Gas Temperature (K) | Evaporation rate (× 10$^{-12}$ mol/s) | Evaporation time (μs) | Drop temperature (K) | Mobility diameter (nm) | GSD |
| 0.01 | 298 | 0.38 | 14.4 | 274.5 | 47 ± 4 | 1.8 |
| | 383 (Pulse) | 1.79 | 3.1 | 299.2 | 56 ± 6 | 1.6 |
| 0.1 | 298 | 0.39 | 14.1 | 274.5 | 56 ± 5 | 1.8 |
| | 383 (Pulse) | 1.82 | 3.0 | 299.2 | 59 ± 3 | 1.6 |
| 1 | 298 | 0.40 | 13.7 | 274.5 | 85 ± 2 | 1.7 |
| | 383 (Pulse) | 1.89 | 2.9 | 299.2 | 116 ± 7 | 1.5 |
| 10 | 298 | 0.44 | 12.5 | 274.6 | 115 ± 11 | 1.7 |
| | 383 (Pulse) | 2.07 | 2.6 | 299.5 | 183 ± 12 | 1.6 |

Results are for 300 nm diameter solution drop of stearic acid in cyclohexane solutions at gas temperatures of 298 K and 383 K (pulse), of varying concentrations, 0.01 mg · cm–3, 0.1 mg · cm–3, 1 g · cm–3 and 10 mg · cm–3 and corresponding experimental measurement of particle mobility diameter using SMPS.

This disclosure therefore relates to a single step method for producing thermolabile nanoparticles of lipids and biopolymers with controlled diameter ranging from 50 to 500 nm which comprises the steps of pumping as aerosol of a precursor solution of lipid/biopolymers in an organic solvent, through a pulse-heat aerosol reactor to control droplet evaporation followed by quenching to produce nanoparticles of controlled size, morphology and crystallinity.

Mean mobility diameter of nanoparticles thus produced will be directly proportional to the rate of evaporation and concentration of the lipid in solution. Higher evaporation and higher concentration result in larger mobility particle size and crystallinity.

This disclosure also relates to a system for carrying out the above method which comprises a pulse-heating zone, connected to a perforated diluter and isoaxial sampler, said system maintaining laminar flow of aerosol introduced there into through an atomizer and said perforated diluter having means to supply a gas there into in a regulated manner.

Obvious equivalents are included in the description and the appended claims.

The invention claimed is:

1. A method for production of thermolabile nanoparticles from thermolabile biocompatible matrix material(s) selected from lipids, biopolymers, and proteins, optionally with therapeutic, cosmetic or protein active agents, comprising of the following steps:
   (a) atomizing a solution of the thermolabile, biocompatible matrix material(s) in aqueous or organic solvent(s), with said active agents, by mixing the solution with carrier gas using an atomizer to create droplets from the solution, wherein solute concentration in the solution ranges from 0.001 mg/ml to 10 mg/ml,
   (b) suspending said droplets in said carrier gas, wherein the carrier gas is selected from the group consisting of nitrogen gas or inert gas,
   (c) passing the droplets suspended in carrier gas from the atomizer to a pulse-heat zone of a pulse-heat aerosol reactor and subjecting said carrier gas with droplets, suspended therein, to pulse heating for controlled evaporation in the pulse-heat zone of the pulse-heat aerosol reactor to form a heated aerosol comprising the suspended nanoparticles and carrier gas under predetermined heat pulse of controlled magnitude and duration comprising exposing the suspended droplets to heating at a temperature in the range of 25° C. to 110° C. for a pulse duration between 0.1 to 1 seconds, to achieve control over nanoparticle properties,
   (d) passing the aerosol formed in step c) along with a gas stream line through a quenching zone to cool the aerosol containing the suspended nanoparticles formed in step c by dilution with cooling gas selected from nitrogen gas or an inert gas, to prevent prolonged heating and thermal damage,
   (e) collecting the nanoparticles produced.

2. The method according to claim 1, wherein the nanoparticles produced are of controlled size, morphology or structure, crystallinity and controlled-release properties.

3. The method as claimed in claim 1, wherein mobility diameter of the nanoparticles is in the range of 50 nm to 200 nm.

4. The method as claimed in claim 1, wherein the nanoparticles have a narrow particle size distribution with geometric standard deviation smaller than 1.8.

5. The method as claimed in claim 1, wherein nanoparticles have solid, hollow or shell-like morphology.

6. The method as claimed in claim 1, wherein nanoparticles have controlled crystallinity, ranging from 10% to 100%.

7. The method as claimed in claim 1, wherein mobility diameter of the nanoparticles is directly proportional to the rate of evaporation and concentration of solute in the precursor solution.

8. The method as claimed in claim 1, wherein the matrix material(s) is/are at least one lipid selected from the group consisting of fatty acids, triglycerides, saturated lipids, synthetic lipids, fats, waxes, and combinations thereof.

9. The method as claimed in claim 1, wherein said organic solvent(s) have differing vapor pressures ranging from about 100 Pa to about 100,000 Pa.

10. The method as claimed in claim 1, wherein the organic solvent is selected from the group consisting of hydrocarbon, halogenated hydrocarbon, alcohol, ketone and ester.

11. The method as claimed in claim 1, wherein said organic solvents are selected from the group consisting of cyclohexane, chloroform and dichloromethane.

12. The method as claimed in claim 1, wherein active agents, selected from the group consisting of drugs, proteins, peptides, nucleic acids, steroids and combinations thereof, are added to the aerosol solution for encapsulation, loading or coating.

13. The method as claimed in claim 1, wherein the active agent(s) is a therapeutic, cosmetic or diagnostic agent.

14. The method as claimed in claim 1, wherein the nanoparticles are collected using a particle collection system selected from the group consisting of an electrostatic precipitator (dry/wet), a cyclone, a filter, a settling chamber, and an impactor.

15. The method as claimed in claim 1, wherein the heat pulse consists of heat to the droplets suspended in carrier gas.

16. The method as claimed in claim 1, wherein the cooling gas is only added to the nanoparticles suspended in carrier gas to enable the quenching.

* * * * *